United States Patent [19]

Dunn

[11] 4,278,670

[45] Jul. 14, 1981

[54] 7-ALPHA-OXYIMINOACYLCEPHALOSPORINS

[75] Inventor: George L. Dunn, Wayne, Pa.

[73] Assignee: SmithKline Corporation, Philadelphia, Pa.

[21] Appl. No.: 704,159

[22] Filed: Jul. 12, 1976

[51] Int. Cl.$^3$ .................. A61K 31/545; C07D 501/56
[52] U.S. Cl. ...................................... 424/246; 544/21; 544/26; 544/27
[58] Field of Search .................. 260/243 C; 424/246; 544/21, 26, 27

[56] References Cited

U.S. PATENT DOCUMENTS

| | | | |
|---|---|---|---|
| 3,812,110 | 5/1974 | Lee et al. | 260/243 C |
| 3,966,717 | 6/1976 | Cook et al. | 260/243 C |
| 3,971,778 | 7/1976 | Cook et al. | 260/243 C |
| 3,974,153 | 8/1976 | Cook et al. | 260/243 C |

FOREIGN PATENT DOCUMENTS 6916151 4/1971 Netherlands ......................... 260/243 C

OTHER PUBLICATIONS

Glaxo, Chemical Abstracts, (1974), vol. 81: 37,558m, 169,551p.
Glaxo, Chemical Abstract, (1975), vol. 83: 43,354z, 179,0825.

*Primary Examiner*—Paul M. Coughlan, Jr.
*Attorney, Agent, or Firm*—William H. Edgerton; Richard D. Foggio; Alan D. Lourie

[57] ABSTRACT

New semisynthetic cephalosporins having antibacterial activity are described. The structures of the new compounds are characterized by having an α-oxyimino group in the 7-acetamidomoiety plus a carboxyalkyltetrazolylthiomethyl group at position 3.

15 Claims, No Drawings

7-ALPHA-OXYIMINOACYLCEPHALOSPORINS

This invention comprises a new series of cephalosporin compounds having antibacterial activity which are characterized by structures combining an α-oxyimino group in the 7-acetamido portion with a carboxyalkyl-tetrazolylthiomethyl substituent at position 3 of the structures.

These compounds have potent antibacterial activity against both gram-positive and gram-negative organisms, especially upon parenteral administration. A further part of this invention comprises methods and compositions for inducing antibacterial activity in infected subjects.

Prior art patents (for example, German Pat. Nos. 2,223,375 and 2,204,060) describe a large number of compounds among which are compounds having structures with an α-oxyiminoacyl at position 7 and a tetrazolethiomethyl at position 3.

The compounds of this invention are represented by the following structural formula:

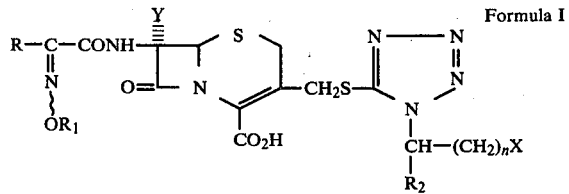

Formula I in which:
R is thienyl, furyl or phenyl optionally substituted as known in the cephalosporin art such as hydroxy, halo such as bromo, chloro or fluoro, nitro, ureido, methoxy, methylthio or trifluoromethyl on the phenyl and methyl or ethyl on the furyl or thienyl ring;
$R_1$ is hydrogen, lower alkyl such as from 1-6 carbon atoms, benzyl, phenethyl, thienylmethyl or furylmethyl;
$R_2$ is hydrogen or methyl;
n is an integer from 0-9;
X is carboxy ($-CO_2H$), carbamyl ($-CONH_2$), methylcarbamyl or dimethylcarbamyl; and
Y is hydrogen or methoxy.

A subgeneric group of this invention is represented by the compounds of Formula I in which R is thienyl, furyl or phenyl; $R_1$ is hydrogen or lower alkyl especially methyl or ethyl; $R_2$ is hydrogen; X is carboxy or carbamyl; n is 0-4 and Y is hydrogen or methoxy. More specifically of interest are compounds of Formula I in which R is furyl; $R_1$ is hydrogen, methyl or ethyl; $R_2$ is hydrogen; n is 0-3; X is carboxy or carbamyl; and Y is hydrogen or methoxy.

The attachment of the heteroaryl of the group in the 7-acylamino moiety is either at the α or β position of said hetero group.

Also covered in this invention are the pharmaceutically acceptable nontoxic derivatives of the compounds described above: the salts, easily hydrolyzed esters at either carboxy or hydroxy groups of the compounds of structure I, hydrates or alcoholates. As examples of these one skilled in the art would be able to prepare and use the alkali metal salts such as sodium or potassium salts, the alkaline metal salts such as calcium, ammonium salts, organic amine salts such as procaine or dibenzylethylene diamine salts or the easily hydrolyzed esters such as t-butyl, trichloroethyl, benzyl, p-methoxy benzyl or benzyloxy esters. For other derivatives see German Pat. No. 2,204,060.

The alkali metal salts are preferred especially the sodium or potassium salts with their hydrates.

The compounds of Formula I may exist as syn (Z) or anti (E) isomers at the imino point in the structure or mixtures thereof. The syn-isomers are preferred. The configuration of the oximes is carried through the synthetic procedure from the substituted glyoxylic acid starting material.

The compounds of Formula I are prepared by N-acylation of an appropriate 7-amino-3-(carboxylatedtetrazolylthiomethyl) cephalosporin nucleus of Formula II:

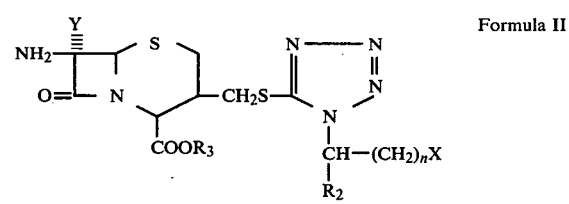

Formula II in which Y, $R_2$, n and X are as in Formula I and $R_3$ is hydrogen or the alcoholic portion of a carboxy protecting ester group, with an appropriate acylating agent followed by removal of the protective groups when present. The carboxylic acid group of the acylating agent, α-oxyiminoarylacetic acid, is activated by any of the standard methods such as conversion to the mixed anhydride, acid chloride or activated ester. In addition, a reagent such as dicyclohexylcarbodiimide or carbonyldiimidazole can be used provided that the carboxyl groups on the cephem nucleus are protected with an easily removable protecting group such as benzhydryl, t-butyl, trichloroethyl, benzyl, benzyloxymethyl, p-nitrophenyl, p-methoxyphenyl, p-methoxybenzyl or p-nitrobenzyl ester. Also the hydroxyl portion of the oxyimino acylating agent may be optionally protected during the reaction for example by a dichloroacetyl group (see German Pat. No. 2,204,060).

Alternatively, the compounds of Formula I are prepared by a displacement reaction at the 3-position of a known 7-(α-oxyiminoarylacetamido)cephalosporanic acid (see German Pat. No. 2,223,375 published Nov. 23, 1972), with the desired carboxy substituted tetrazole-thiol followed by subsequent removal of any protective group(s) present. The substituted tetrazole thiols thusly used are of the formula:

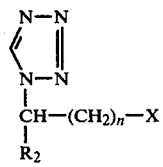

Formula III in which $R_2$, n and X are as described above.

The protective groups used in these procedures can be removed according to methods well known to the art, such as with trifluoroacetic acid when the t-butyl group is used.

The acylating agents used as starting materials are either known or prepared by known methods.

As stated above the 7-amino-3-carboxy-substituted tetrazolylthiomethyl cephalosporin starting materials of Formula II are prepared from a displacement reaction of a 7-aminocephalosporanic acid and a substituted tetrazole thiol of Formula III.

The substituted tetrazole thiols of Formula III where X is carboxy are prepared by reaction of an isothiocyanate, for example ethyl isothiocyanoacetate, or an N-alkyl dithiocarbamate, such as methyl 2-carboxyethyldithiocarbamate, with an azide such as sodium azide. When X is carbamyl or its N-alkyl substituted derivatives, the tetrazole thiols of Formula III are prepared from the corresponding tetrazole thiols where X is carboxy by standard methods for the preparation of amides from acids, for example, by reaction of a tetrazole thiol where X is carboxy with 1,1-carbonyldiimidazole and an amine or by conversion of the tetrazole thiol where X is carboxy to the corresponding acid chloride with subsequent reaction of the acid chloride with the appropriate amine. The tetrazole thiols of Formula III are also prepared by conversion of a suitably substituted hydroxy tetrazole to the corresponding thiol by the method of Hoover and Day [J. Amer. Chem. Soc., 78:5832 (1956)].

The compounds of Formula I have very potent antibacterial activity with minimal inhibitory concentrations (MIC's) ranging from 0.2 to >200 μg./ml. in vitro testing. Results with a representative compound are given in Table 1.

administration may be orally but is preferably by parenteral injection such as subcutaneously, intramuscularly or intravenously. The injection of suitably prepared sterile solutions or suspensions containing an effective, nontoxic amount of the new cephalosporin compound is the most effective route of administration.

The compounds of Formula I are formulated and administered in the same manner as other cephalosporins. The dosage regimen comprises administration, preferably by injection, of an active but nontoxic quantity of a compound of Formula I selected from the dosage unit range of from 50 to 500 mg. with the total daily dosage regimen being from 400 mg. to 6 g. The precise dosages are dependent upon the age and weight of the subject and on the infection being treated and can be determined by those skilled in the art based on the data disclosed herein compared with that available to the art attained with known cephalosporins as outlined herebefore.

The following examples are designed to illustrate the methods of preparing the compounds claimed here.

PREPARATION 1

β-Alanine (17.8 g., 0.2 mol.) was added to a solution of 22.4 g. (0.4 mol.) of potassium hydroxide in 500 ml of water at 25° C. Carbon disulfide (12.2 ml., 0.2 mol.) was added and the reaction mixture was refluxed for three hours. The mixture was cooled, 28.4 g. (0.2 mol.) of methyl iodide and 500 ml. of ethanol were added and

TABLE 1

| | MIC (μg./ml.) in vitro | | | | | | | | | |
|---|---|---|---|---|---|---|---|---|---|---|
| | G+ S. Aureus HH 127 | G+ S. Aureus SK 23390 | G+ S. villaluz SK 70390 | G+ Strep. Faecalis HH 34358 | G− E. coli SK 12140 | G− E. coli HH 33779 | G− Kleb. pneumoniae SK 2400 | G− Kleb. pneumoniae SK 1200 | G− Salmonella ATCC 12176 | G− Pseudo Aeruginosa HH 63 |
| Example 1 | 3.1 | 1.6 | >200 | 50 | 1.6 | 3.1 | 0.8 | 0.8 | 0.8 | 200 |
| Cefazolin | 0.4 | 0.2 | 200 | 6.3 | 0.8 | 0.8 | 0.8 | 0.8 | 0.8 | >200 |
| Cephalothin | 0.2 | 0.2 | 50 | 12.5 | 3.1 | 6.3 | 3.1 | 1.6 | 0.8 | >200 |
| Cefuroxim | 0.8 | 1.6 | >200 | 2.5 | 6.3 | 6.3 | 3.1 | 3.1 | 3.1 | >200 |

| | MIC (μg./ml.) in vitro | | | | |
|---|---|---|---|---|---|
| | G− Serratia Marcescens ATCC 13880 | G− Proteus morgani 179 | G− Entero. aerogenes ATCC 13048 | G− Entero. cloacae HH 31254 | G− P. Mirabils PM 444 |
| Example 1 | 3.1 | 1.6 | 3.1 | 1.6 | 0.2 |
| Cefazolin | 100 | 100 | 1.6 | 0.8 | 3.1 |
| Cephalothin | >200 | >200 | 12.5 | 6.3 | 3.1 |
| Cefuroxim | 12.5 | 50 | 6.3 | 3.1 | 1.6 |

For comparison with known used compounds, data for cefuroxime, cefazolin and cephalothin are included. The results (ED50, S.C.) in mouse protection against E. coli 12140 with the compound of Example 1 was 4.4 mg./kg.; cefuroxime, 6.25; cefazolin, 6.25.

It will be noted that the preferred compound whose data is presented above is especially active against Serratia, Proteus and a number of Gram negative organisms.

Pharmaceutical compositions having antibacterial activity which comprise a pharmaceutical carrier containing an active but nontoxic quantity of a compound of Formula I as well as methods of combatting bacterial infections by administering such a composition to an infected host in a nontoxic amount sufficient to combat such infections are also objects of this invention. The the resulting mixture was stirred for 30 minutes. The precipitate was collected by filtration, the filtrate was concentrated and the aqueous residue was combined with the solid material and brought to pH 8.5-9 by addition of 10% aqueous sodium hydroxide. The resulting suspension was extracted with ethyl acetate. Ethyl acetate was added to the aqueous phase which was then acidified to pH 1.5 with 6 N hydrochloric acid. The layers were separated and the aqueous phase was extracted again with ethyl acetate. The ethyl acetate extracts were combined, dried (MgSO₄) and evaporated to dryness to give methyl 2-carboxyethyldithiocarbamate.

To a mixture of 25.37 g. (0.143 mol.) of methyl 2-carboxyethyldithiocarbamate and 5.6 g. (0.143 mol.) of sodium hydroxide in 210 ml. of water was added 9.25 g. (0.143 mol.) of sodium azide. The reaction mixture was refluxed for one hour then cooled, diluted with 100 ml. of ether and acidified to pH 1.7. The layers were separated, the aqueous phase was extracted with ether and the combined extracts were dried (MgSO$_4$) and evaporated to dryness to give a residue which was recrystallized from acetone-chloroform to give 1-(2-carboxyethyl)tetrazole-5-thiol, m.p. 158°–160° C.

The amide intermediates are prepared from the acids by standard reactions such as using 1,1-carbonyldiimidazole with the desired amine in tetrahydrofuran.

Other similar tetrazolethiols are described in Belgian Pat. No. 837,030 or Belgian Pat. No. 832,725 such as 1-carboxymethyltetrazole-5-thiol, m.p. 178°–179° C.; 1-N-methylcarbamoylmethyltetrazole-5-thiol, m.p. 137°–140° C.; 1-N,N-dimethylcarbamoylmethyltetrazole-5-thiol, m.p. 190°–200° C.; 1-carbamoylmethyltetrazole-5-thiol, m.p. 200° C.; 1-(2-carbamoylethyl)tetrazole-5-thiol, m.p. 181°–182° C.; 1-(3-carboxypropyl)-tetrazole-5-thiol, m.p. 99°–101° C.; 1-(3-carbamylpropyl)tetrazole-5-thiol, m.p. 133°–136° C.; 1-(5-carboxypentyl)tetrazole-5-thiol, m.p. 100°–100.5° C.; 5-(5-carbamylpentyl)tetrazole-5-thiol, m.p. 155°–157° C.; 1-(10-carboxydecyl)tetrazole-5-thiol, m.p. 95°–98° C.; 1-(2-carboxyl-1-methylethyl)tetrazole-5-thiol, m.p. 169°–172° C.

PREPARATION 2

A solution of 1-(2-carbamylethyl)tetrazole-5-thiol (10.4 g., 0.06 mol.) in 120 ml. of acetone was added to a warm (45°) solution of 10.9 g. (0.04 mol.) of 7-aminocephalosporanic acid in a mixture of 220 ml. of water, 50 ml. of acetone and 8.4 g. (0.01 mol.) of sodium bicarbonate. The temperature was raised to 65° and the pH maintained at 7.4–7.6 by addition of aqueous sodium carbonate solution. After three hours, the reaction mixture was cooled to 10° and adjusted to pH 3.5 by addition of dilute hydrochloric acid. The resulting solid was collected by filtration, washed with water and acetone and suspended in 95 ml. of 1.5 N hydrochloric acid. The acid suspension was stirred at 25° for five hours, filtered and the pH of the filtrate was adjusted to 3.5 by addition of solid sodium bicarbonate. The solid was collected by filtration and washed with water and acetone to give 7-amino-3-[1-(2-carbamylethyl)-tetrazol-5-ylthiomethyl]-3-cephem-4-carboxylic acid.

Substituting equimolar quantities of the functionally substituted tetrazole-5-thiols from Preparation 1 in the above reaction gives the corresponding 7-amino-3-[1-(carboxy or carbamylalkyl)-tetrazol-5-ylthiomethylthiomethyl]-3-cephem-4-carboxylic acids.

PREPARATION 3

To a suspension of 19.3 g. (0.05 mol.) of 7-amino-3-[1-(2-carbamoylethyl)tetrazol-5-ylthiomethyl]-3-cephem-4-carboxylic acid in 500 ml. of dry methylene chloride is added in one portion 30.0 g. (0.15 mol.) of O-t-butyldiisopropylpseudourea in 50 ml. of methylene chloride and the mixture is stirred at ambient temperature for 24 hours. The precipitate is removed by filtration and the filtrate is evaporated to give a residue which is taken up in 200 ml. of benzene and filtured again. The filtrate is extracted with three 100 ml. portions of cold 1 N hydrochloric acid. The aqueous extracts are layered with ethyl acetate and the pH is adjusted to 7.5 by addition of solid sodium bicarbonate. The organic layer is separated and the aqueous phase is extracted with two 150 ml. portions of ethyl acetate. The combined extracts are dried (MgSO$_4$), filtered and evaporated to dryness to give 7-amino-3-[1-(2-carbamoylethyl)tetrazol-5-ylthiomethyl]-3-cephem-4-carboxylic acid t-butyl ester.

A solution of 1.76 g. (4 mmol.) of 7-amino-3-[1-(2-carbamoylethyl)tetrazol-5-ylthiomethyl]-3-cephem-4-carboxylic acid t-butyl ester and 0.94 g. (4 mmol.) of 3,5-di-t-butyl-4-hydroxybenzaldehyde in 150 ml. of dry benzene is refluxed for ca. 4 hours under a Dean-Stark trap until no more water separates. The solution is evaporated under reduced pressure to give a residue which is dissolved in 150 ml. of 1,2-dichloroethane and cooled to 0°–5° in an ice bath. Freshly prepared lead dioxide (5 g.) is added in 1 g. portions over 30 minutes and the reaction is stirred in the cold until complete consumption of starting material is shown by thin layer chromatography. The mixture is then filtered through Celite and the filter cake is washed with two 30 ml. portions of cold 1,2-dichloroethane. The filtrate is treated with 30 ml. of dry methanol (distilled from magnesium) and the reaction mixture is stirred at ambient temperature until complete consumption of the intermediate and formation of a new product are shown by thin layer chromatography. The reaction mixture is evaporated to dryness and the residue is taken up in 50 ml. of methanol and treated with 4.0 g. of Girard reagent T. This solution is stirred at ambient temperature for 3 hours, evaporated under vacuum to a solid residue and partitioned between 150 ml. of ethyl acetate and 100 ml. of 20% aqueous sodium chloride solution. The organic phase is washed with three 100 ml. portions of 10% aqueous sodium chloride, two 100 ml. portions of water and 100 ml. of a saturated sodium chloride solution. The organic phase is dried (MgSO$_4$), filtered and evaporated to dryness to give 7$\beta$-amino-7$\alpha$-methoxy-3-[1-(2-carbamoylethyl)tetrazol-5-ylthiomethyl]-3-cephem-4-carboxylic acid t-butyl ester.

PREPARATION 4

To a suspension of 19.3 g. (0.05 mol.) of 7-amino-3-[1-(2-carboxyethyl)tetrazol-5-ylthiomethyl]-3-cephem-4-carboxylic acid in 500 ml. of methylene chloride was added over a 30 minute interval a solution of 60.0 g. (0.3 mol.) of O-t-butyldiisopropylpseudourea in 100 ml. of methylene chloride. The mixture was stirred at ambient temperature of 72 hours. The precipitate was removed by filtration and the filtrate was evaporated to a residue which was taken up in 200 ml. of benzene and filtered again. The filtrate was extracted with three 100 ml. portions of cold 1 N hydrochloric acid. The aqueous extracts were layered with ethyl acetate and the pH was adjusted to 7.5 by addition of solid sodium bicarbonate. The organic layer was separated and the aqueous phase extracted with two 150 ml. portions of ethyl acetate. The combined extracts were dried (MgSO$_4$), filtered and evaporated to dryness to give 6.1 g. of 7-amino-3-[1-(2-t-butoxycarbonylethyl)tetrazol-5-ylthiomethyl]-3-cephem-4-carboxylic acid t-butyl ester.

A solution of 1.19 g. (2.4 mmol.) of 7-amino-3-[1-(2-t-butoxycarbonylethyl)tetrazol-5-ylthiomethyl]-3-cephem-4-carboxylic acid t-butyl ester and 0.56 g. (2.4 mmol.) of 3,5-di-t-butyl-4-hydroxybenzaldehyde in 100 ml. of dry benzene was refluxed for 4 hours under a Dean-Stark trap. The solution was evaporated under reduced pressure to leave a residue which was dissolved in 100 ml. of 1,2-dichloroethane and cooled to ca. 5° in an ice bath. Three grams of freshly prepared lead dioxide was added in portions over 20 minutes until the starting material was completely consumed. The mixture was filtered through Celite and the filter cake was washed with two 20 ml. portions of cold, 1,2-dichloroethane. The filtrate was treated with 25 ml. of methanol (distilled from magnesium) and the reaction mixture was allowed to stand at room temperature until complete consumption of the oxidized intermediate and formation of a new slower-moving product was shown by thin layer chromatography (ca. 3 hours). The mixture was evaporated to yield a brown semi-solid which was dissolved in 30 ml. of methanol and treated with 2.5 g. of Girard reagent T (trimethylaminoacetohydrazide chloride). The reaction mixture was stirred at room temperature for 3 hours, then evaporated to give a solid residue which was partitioned between 100 ml. of ethyl acetate and 100 ml. of 20% sodium chloride solution. The organic phase was washed with three 100 ml. portions of 10% sodium chloride solution, two 100 ml. portions of water and 100 ml. of a saturated sodium chloride solution. The organic phase was dried (MgSO$_4$), filtered and evaporated to dryness to give 7$\beta$-amino-7$\alpha$-methoxy-3-[1-(2-t-butoxycarbonylethyl)-tetrazol-5-ylthiomethyl]-3-cephem-4-carboxylic acid t-butyl ester.

EXAMPLE 1

7[Syn-2-methoxyimino-2-$\alpha$-furylacetamido]-3-[1-(2-carboxyethyl)tetrazol-5-ylthiomethyl]-3-cephem-4-carboxylic acid, disodium salt A solution of syn-2-methoxyimino-2-furylacetyl chloride (1.4 g, 7.5 mmol.) in 100 ml. of acetone was added gradually to a cold ($-10°$ C.) stirred solution of 7-amino-3-[1-(2-carboxyethyl)tetrazol-5-ylthiomethyl]-3-cephem-4-carboxylic acid (2.3 g, 6.0 mmol.) in 100 ml. of water and 100 ml. of acetone containing sodium bicarbonate (1.63 g, 19.4 mmol.). After the addition was complete the pH of the mixture was adjusted to 7.6–7.8 with dilute bicarbonate and stirring was continued at $-10°$ C. for 30 minutes and finally at ambient temperature for 1.5 hr. After evaporating the acetone in vacuo the mixture was extracted with ethyl acetate (discarded), the pH of the aqueous phase adjusted to 2.0 and extracted with ethyl acetate. Evaporation of the dried (magnesium sulfate) ethyl acetate extract gave 2.3 g. of crude product. This was chromatographed on a column of silica gel and the product was eluted with chloroform-methanol-formic acid (90:10:1). The material obtained from the column was dissolved in dilute sodium bicarbonate and extracted at several pH intervals with ethyl acetate. The organic extracts between pH 4.5 and 2.5 were combined, dried and evaporated. The residue was dissolved in methanol, treated with sodium methoxide in methanol and diluted with ether to give 0.43 g. of the title compound.

Potassium methoxide treatment gives the dipotassium salt.

Anal. Calc'd for $C_{19}H_{17}Na_2N_7O_8S_2 \cdot 1.5 H_2O \cdot 0.3 CH_3OH \cdot 0.12 Et_2O$: C, 37.88; H, 3.60; N, 15.63; Found: C, 37.66; H, 3.84; N, 15.31.

EXAMPLE 2

7-(Syn-2-hydroxyimino-2-phenylacetamido)-3-(1-carboxymethyltetrazol-5-ylthiomethyl)-3-cephem-4-carboxylic acid, disodium salt A solution of 0.013 mol. (5.25 g.) of 7-(syn-2-hydroxyimino-2-phenylacetamido)cephalosporanic acid (syn.) (German Pat. No. 2,204,060) and 0.015 mol. of 1-carboxymethyl-tetrazole-5-thiol disodium salt in 100 ml. of water containing sodium bicarbonate (0.015 mol.) is heated to 70° C. for 5 hours. An additional gram of the cephalosporanic acid is added after 1.5 hours reaction. The pH is maintained at 7.4–7.6 by addition of dilute bicarbonate solution. After cooling to room temperature the reaction mixture is extracted with ethyl acetate. The aqueous layer is acidified to pH 2 with dilute hydrochloric acid, then extracted with ethyl acetate. The acidic aqueous layer is neutrazlized to pH 7.0 with bicarbonate solution then chromatographed over a cross linked copolymer of styrene-divinyl benzene (XAD-4, Rohm and Haas Co., Philadelphia, Pa.) with elution with aqueous methanol to give the title compound.

EXAMPLE 3

7-[Syn-2-ethoxyimino-2$\alpha$-furylacetamido]-7-$\alpha$-methoxy-3-[1-(2-carbamoylethyl)-tetrazole-5-ylthiomethyl]-3-cephem-4-carboxylic acid To a solution of 6.0 mmol. of 7$\beta$-amino-7$\alpha$-methoxy-3-[1-(2-carbamoylethyl)tetrazole-5-ylthiomethyl]-3-cephem-4-carboxylic acid, t-butyl ester and 6.5 mmol. of dicyclohexylcarbodiimide in dry methylene chloride at 0°–20° C. one adds a solution of syn-2-ethoxyimino-2-furylacetic acid in dry methylene chloride. After stirring at room temperature for 6 hours, the mixture is filtered. The filtrate is washed with 2 N hydrochloric acid, bicarbonate solution, water, then salt solution. The organic layers are dried to give the ester.

The ester is dissolved in trifluoroacetic acid and, allowed to stand at room temperature for 3 hours, then evaporated to dryness. The residue is taken up in ethyl acetate and extracted into sodium bicarbonate solution. The bicarbonate phase is acidified to pH 2, extracted with ethyl acetate and the organic layers washed with water, dried and evaporated to give the title product.

EXAMPLE 4

Substituting in Example 1 equimolar quantities of the 7-amino-3-(1-substituted tetrazol-5-ylthiomethyl)-3-cephem-4-carboxylic acid (A) and 2-oxyimino-2-arylacetylchloride (B) or an equivalent mixed anhydride gives the following end products:

| | A | B | Product |
|---|---|---|---|
| 1. | Y = H; X = —CO$_2$H; | anti R = phenyl; | 7-[anti-2-methoxy-imino-2-phenyl-acetamido]-3-[1-(2-carboxy-1-methylethyl)-tetrazol-5-ylthio-methyl]-3-cephem-4-carboxylic acid as the disodium salt. |
| | n = 1; R$_2$ = methyl | R$_1$ = methyl | |

| A | B | Product |
|---|---|---|
| 2. Y = H;<br>X = —(CON(CH$_3$)$_2$;<br>n = O; R$_2$ = H | syn R = α-thienyl;<br>R$_1$ = methyl | 7[syn-2-methoxyimino-2-α-thienylacetamido]-3-[1-N,N-dimethyl-carbamylmethyl-tetrazol-5-ylthiomethyl]-3-cephem-4-carboxylic acid, sodium salt. |
| 3. Y = H; X = —CO$_2$H;<br>n = 2; R$_2$ = H | syn R = β-furyl;<br>R$_1$ = butyl | 7-[syn-2-butoxyimino-2-β-furylacetamido]-3-[1-(3-carboxypropyl-tetrazol-5-ylthiomethyl]-3-cephem-4-carboxylic acid, as the dipotassium salt. |
| 4. Y = H; X = —CONHCH$_3$;<br>n = O; R$_2$ = H | syn R = α-furyl;<br>R$_1$ = benzyl | 7-[syn-2-benzyloxyimino-2-α-furylacetamido]-3-[1-methyl-carbamylmethyl-tetrazol-5-ylthiomethyl]-3-cephem-4-carboxylic acid, sodium salt. |
| 5. Y = H; X = —CONH$_2$;<br>n = 1; R$_2$ = H | syn R = phenyl;<br>R$_1$ = ethyl | 7-[syn-2-ethoxyimino-2-phenylacetamido]-3-[1-(2-carbamylethyl)-tetrazol-5-ylthiomethyl]-3-cephem-4-carboxylic acid, sodium salt. |

EXAMPLE 5

Substituting in Example 2 equimolar quantities of the 7-(2-oxyimino-2-arylacetamido)-cephalosporanic acid (A) and the substituted tetrazol-5-thiol (b) gives the following end products:

| A | B | Product |
|---|---|---|
| 1. syn R = α-thienyl;<br>R$_1$ = α-thienylmethyl;<br>Y = H | X = —CO$_2$H; n = 4;<br>R$_2$ = H | 7-[syn-2-α-thienyl-methoxyimino-2-α-thienylacetamido]-3-[1-(5-carboxypentyl)-tetrazol-5-ylthio-methyl]-3-cephem-4-carboxylic acid, disodium salt. |
| 2. syn R = α-furyl;<br>R$_1$ = α-furylmethyl;<br>Y = H | X = —CO$_2$H; n = 2;<br>R$_2$ = H | 7-[syn-2-α-furylmethoxy-imino-2-α-furyl-acetamido]-3-[1-(3-carboxypropyl)-tetrazol-5-ylthiomethyl]-3-cephem-4-carboxylic acid disodium salt. |
| 3. syn R = α-thienyl;<br>R$_1$ = tert-butyl;<br>Y = H | X = CONH$_2$;<br>n = 1; R$_2$ = H | 7-[syn-2-tert.-butoxy imino-2-α-thienyl-acetamido]-3-[1-(2-carbamylethyl)-tetrazol-5-ylthiomethyl]-3-cephem-4-carboxylic acid. |

EXAMPLE 6

7β-[syn-2-methoxyimino-2-p-hydroxy-phenylacetamido]-7α-methoxy-3-[1-(2-carboxyethyl)-tetrazole-5-ylthiomethyl]-3-cephem-4-carboxylic acid A mixture of 7 mmol. of 2-methoxyimino-2-p-hydroxyphenylacetic acid (prepared by the method of German Pat. No. 2,223,375), 7 mmol. of 7β-amino-7α-methoxy-3-[1-2-t-butoxycarbonylethyl)-tetrazol-5-ylthiomethyl]-3-cephem-4-carboxylic acid t-butyl ester and 7 mmol. of dicyclohexylcarbodiimide in 100 ml. of dry methylene chloride is stirred for 6 hours. After filtration, the supernatant liquid is evaporated to leave a residue which is taken up in chloroform, washed and dried. The residue therefrom is dissolved in 25 ml. of trifluoroacetic acid and allowed to stand for 1 hour. After evaporation the residue is triturated with ether to give the title product.

Substituting other substituted 2-phenyl-2-oxyimino acetic acids of 2-furyl or thienyl-2-oxyimino-acetic acids in this procedure give variously substituted congeners such as the p-chloro, p-nitro, p-hydroxy-m-chloro, o-methoxy, m,p-dihydroxy, p-ureido in the phenyl series of α-methyl, β-methyl in the furyl or thienyl series.

EXAMPLE 7

An injectable pharmaceutical composition is prepared by adding sterile water or sterile saline solution (2 ml.) to 400 mg. of 7-[syn-2-methoxyimino-2α-furylacetamido)-3-[1-(2-carboxyethyl)tetrazol-5-ylthiomethyl]-3-cephem-4-carboxylic acid, disodium salt.

This preparation may be injected parenterally from 2–5 times daily to an infected patient.

The other compounds described in Examples 1-6 are similarly used.

What is claimed is:

1. An acid compound of the formula:

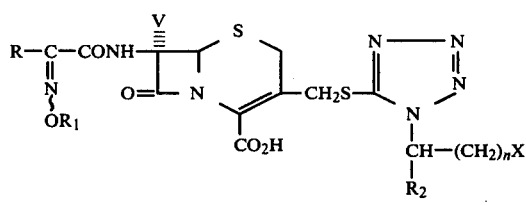

in which:

R is thienyl, furyl or phenyl optionally monosubstituted by hydroxy, halo, methoxy, nitro, ureido, methylthio or trifluoromethyl;

$R_1$ is hydrogen, lower alkyl, benzyl, phenethyl, thienylmethyl or furylmethyl;

$R_2$ is hydrogen or methyl;

n is selected from 0–9;

X is carboxy, carbamyl, N-methylcarbamyl or N,N-dimethylcarbamyl; and

Y is hydrogen or methoxy; or one of its nontoxic pharmaceutically acceptable alkali metal salt, amine salt or easily hydrolyzed ester derivatives.

2. A compound of claim 1 in which the configuration at the imino linkage is syn.

3. A compound of claim 2 in which R is α-furyl.

4. A compound of claim 2 in which X is carboxy.

5. A compound of claim 2 in which R is α-furyl, $R_2$ is hydrogen and X is carboxy.

6. A compound of claim 2 in which R is α-furyl, $R_1$ is hydrogen and $R_2$ is hydrogen.

7. A compound of claim 2 in which R is α-furyl, $R_1$ is lower alkyl of 2–4, $R_2$ is hydrogen and n is 0–2.

8. The compound of claim 1 being 7-[syn-2-methoxyimino-2α-furylacetamido]-3-[1-(2-carboxyethyl)-tetrazol-5-ylthiomethyl]-3-cephem-4-carboxylic acid, or its pharmaceutically acceptable alkali metal salt.

9. The compound of claim 7 in the diacid form.

10. The compound of claim 7 in the disodium salt form.

11. A pharmaceutical composition having antibacterial activity comprising an effective but nontoxic quantity of a compound of claim 1 and a pharmaceutical carrier therefor.

12. A pharmaceutical composition having antibacterial activity comprising an effective but nontoxic quantity of a compound of claim 8 and a pharmaceutical carrier therefor.

13. A method of treating bacterial infections comprising administering parenterally to an infected subject an antibacterially effective and nontoxic quantity of a compound of claim 1.

14. A method of treating bacterial infections comprising administering parenterally to an infected subject an antibacterially effective and nontoxic quantity of a compound of claim 8.

15. A compound having the formula:

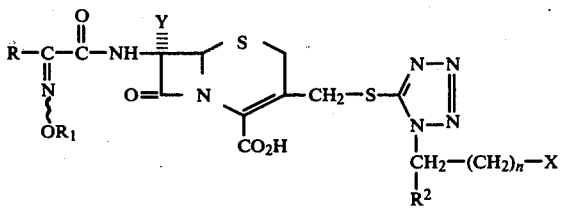

in which:

R is thienyl or furyl;

$R_1$ is hydrogen, lower alkyl, benzyl or phenethyl;

$R_2$ is hydrogen or methyl;

n is 0–9;

X is carboxy, carbamyl, N-methyl carbamyl or N,N-dimethyl carbamyl;

Y is hydrogen or methoxy; and pharmaceutically acceptable salts thereof.

* * * * *